United States Patent [19]

Najer et al.

[11] 4,067,996
[45] Jan. 10, 1978

[54] PHENYLACETIC ACID DERIVATIVES

[75] Inventors: Henry Najer, Paris; Don Pierre René Lucien Giudicelli, Fontenay-sous-Bois; Philippe Michel Jacques Manoury, L'Hay-les-Roses; Jean-Marie Louis Eugéne Roger, Fontenay-aux-Roses, all of France

[73] Assignee: Synthelabo, Paris, France

[21] Appl. No.: 645,351

[22] Filed: Dec. 30, 1975

[30] Foreign Application Priority Data

Dec. 30, 1974 France .................. 74.43223
Sept. 26, 1975 France .................. 75.29474

[51] Int. Cl.² .............. C07C 69/76; A61K 31/215
[52] U.S. Cl. .......................... 424/308; 424/263; 424/267; 424/278; 424/317; 424/324; 260/293.82; 260/295 R; 260/340.9 R; 260/520 C; 260/599; 560/62
[58] Field of Search ............ 260/473 G, 520 C; 424/308

[56] References Cited

U.S. PATENT DOCUMENTS 3,517,050  6/1970  Bolhofer .................. 260/473 G
3,517,051  6/1970  Bolhofer .................. 260/473 G

FOREIGN PATENT DOCUMENTS 1,548,522  12/1968  France .................. 260/473 G Primary Examiner—Jane S. Myers
Attorney, Agent, or Firm—Stevens, Davis, Miller & Mosher

[57] ABSTRACT

The invention provides novel phenylacetic acid derivatives of the formula:

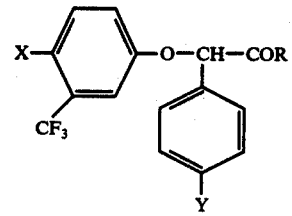

in which X and Y are the same or different and each represents halogen and R represents hydroxyl, alkoxy of 1 to 4 carbon atoms, a radical of formula $R_1$—NH—$C_nH_{2n}$—O—, in which $n$ is an integer from 1 to 4 and $R_1$ is hydrogen or an alkanoyl radical $R_2CO$—, in which $R_2$ is alkyl of 1 to 4 carbon atoms, a radical of formula $R_4NH$—, in which $R_4$ is hydrogen or —$C_mH_{2m}OH$, where $m$ is an integer from 1 to 3, or a radical of formula:

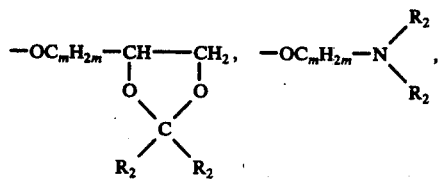

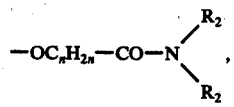

—$OC_mH_{2m}$—$COOR_2$ or —$O(CH_2)_p$—Z radical, where $n$, $m$ and $R_2$ have the meanings given above, $p$ is 0 or 1, and Z is a saturated or unsaturated ring with 6 ring atoms, one of which can be nitrogen, and which can carry from 1 to 3 methyl radicals, and the addition salts which such a derivative which contains a salifiable basic group forms with pharmaceutically acceptable acids and a process for their preparation. These compounds are useful as hypolipaemic and hypocholesterolaemic agents.

4 Claims, No Drawings

PHENYLACETIC ACID DERIVATIVES

The present invention relates to derivatives of phenylacetic acid, their preparation and compositions containing them.

The compounds of the invention have the formula:

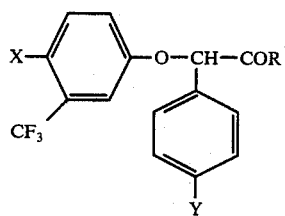

I in which X and Y are the same or different and each represents halogen, especially fluorine or chlorine, and R represents hydroxyl, alkoxy of from 1 to 4 carbon atoms, a radical of formula $R_1-NH-C_nH_{2n}-O-$, in which n is an integer from 1 to 4 and $R_1$ is hydrogen or an alkanoyl radical $R_2CO-$, in which $R_2$ is alkyl of 1 to 4 carbon atoms, a radical of formula $R_4NH-$, in which $R_4$ is hydrogen or $-C_mH_{2m}OH$, where $m$ is an integer from 1 to 3, or a radical of formula:

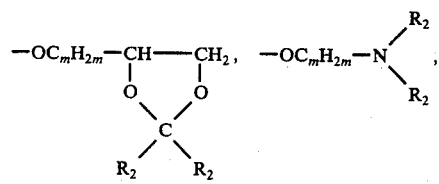

$-OC_mH_{2m}-COOR_2$ or $-O(CH_2)_p-Z$ radical, where $n$, $m$ and $R_2$ are as defined above, p is 0 or 1, and Z is a saturated or unsaturated ring with 6 ring atoms, one of which can be nitrogen, and which can carry from 1 to 3 methyl radicals, and the addition salts which the compounds of formula I, which contain a salifiable basic group, form with pharmaceutically acceptable acids.

The invention particularly relates to compounds in which R is hydroxyl, alkoxy, aminoalkoxy, acylaminoalkoxy, dialkylaminoalkoxy, dialkylaminocarbonyl-alkoxy, alkoxycarbonyl-alkoxy, amino or hydroxyalkylamino, the said alkyl, alkoxy and acyl radicals having from 1 to 4 carbon atoms each.

Especially preferred are those compounds in which X and Y each represent, independently of one another, chlorine or fluorine, and R is hydroxyl, methoxy, ethoxy, 2-acetylamino-ethoxy, 2-hydroxy-ethylamino, 1-methyl-piperidinyl-4-oxy, 3-dimethylaminocarbonyl-propoxy, 3,3,5-trimethyl-cyclohexyloxy, amino, pyridyl-3-methoxy, ethoxycarbonyl-methoxy, 2,2-dimethyl-1,3-dioxolan-4-yloxy or diethylamino-ethoxy.

The compounds of the invention are medicaments which can be used in human and veterinary medicine, in particular as hypolipaemic and hypocholesterolaemic agents.

The compounds of formula I can be prepared by applying known methods, and more particularly by a process which comprises reacting a phenol of formula:

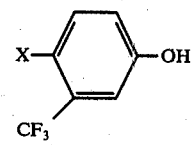

with an alkyl 2-halogeno-2-(p-halogenophenyl)acetate of formula:

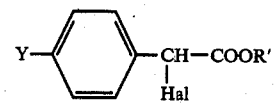

where R' is the same as R but is not $R_4NH-$, Hal is halogen, and Y is as hereinbefore defined, to give a compound of formula I in which R is other than $R_4NH-$, which may then be hydrolysed to give a compound of formula I in which R is hydroxyl, or transesterified, or hydrolysed and then re-esterified, to produce a compound of formula I in which R is alkoxy, $R_1-NH-C_nH_{2n}O-$,

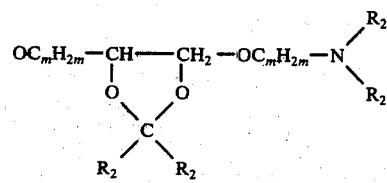

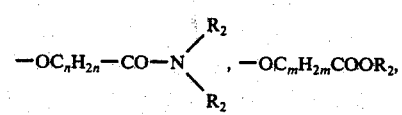

or $-O(CH_2)_p-Z$, or amidified or hydrolysed and then amidified to produce a compound of formula I in which R is $R_4NH-$, and optionally converting any compound of formula I obtained which is a base into a pharmaceutically acceptable acid addition salt thereof.

The acids and the esters of formula (I), may be obtained from the amine of formula (II) in accordance with the following reaction scheme.

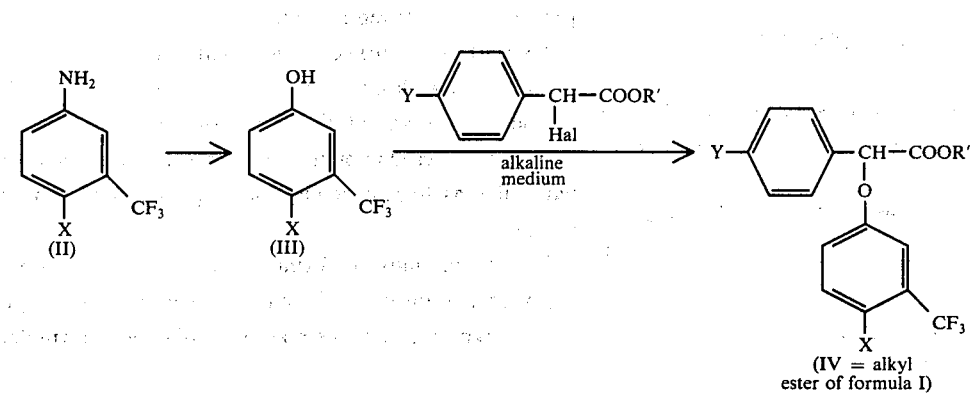

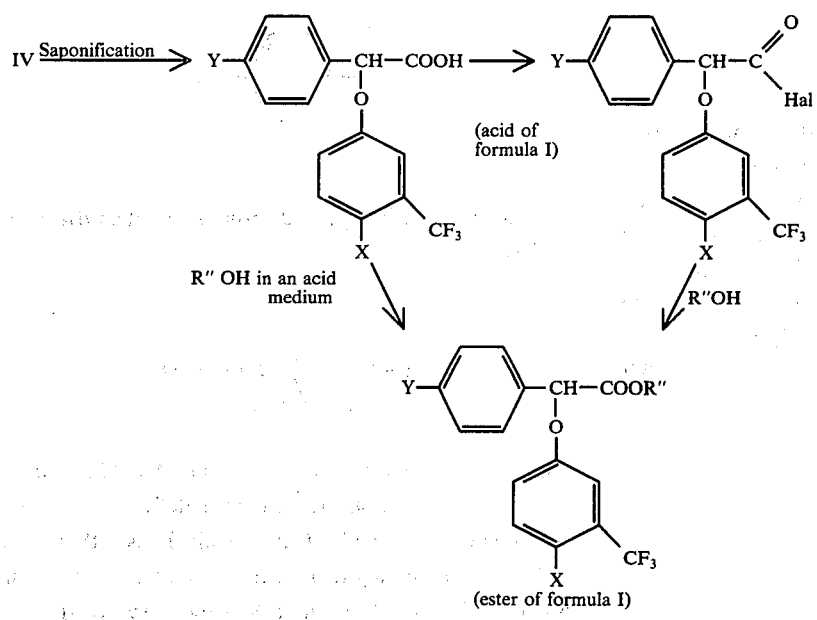

The amine of formula (II) is converted into the phenol by diazotisation in an acid medium. The phenol of formula (III) is condensed with an alkyl 2-halogeno-2-(p-halogenophenyl)-acetate in an alkaline medium, at the reflux temperature of a polar solvent, such as an alcohol, in particular methanol or ethanol. If desired, the ester of formula (IV) is saponified by treatment with an alkali metal hydroxide, followed by acidification, and thereafter, if desired, the acid compound I is esterified either directly, or after conversion to an acid halide, by reacting it with a compound R"OH in an acid medium.

A possible variant of this process consists of directly converting the ester of formula IV to the ester of formula I by transesterification; it is also possible to obtain the acids of formula I or the esters of formula I directly by condensing the phenol of formula (III) with respectively a 2-halogeno-2-(p-halogeno-phenyl)acetic acid of the formula:

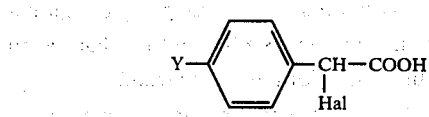

or a corresponding 2-halogeno-2-(p-halogenophenyl-)acetate of the formula:

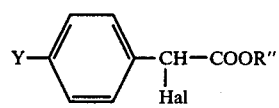

In the reaction scheme, the halogen atoms are preferably chlorine or bromine, R' is an alkyl radical and R" has the same meanings as R, except for $R_4NH$. The other symbols are as previously defined.

The amides of formula I ($R = R_4NH-$) are prepared by amidisation of the corresponding acids of formula 1 in accordance with the equation:

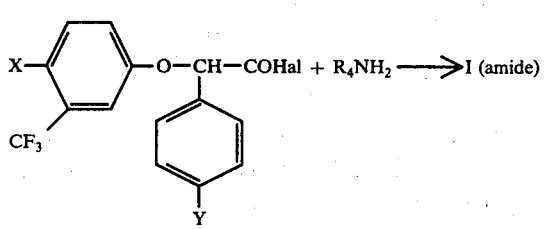

where the halogen is preferably chlorine.

This reaction is advantageously carried out in a non-polar solvent, such as ethyl ether, at a fairly low temperature. If $R_4$ is H, the solvent may be saturated with gaseous ammonia.

The Examples which follow illustrate the invention.

EXAMPLE 1.

Methyl 2-(4-chloro-phenyl)-2-(4-fluoro-3-trifluoromethyl-phenoxy)-acetate

[X = F; Y = Cl; R = CH$_3$O; code number: SL—C.248]

a. 70 g (0.39 mol) of 4-fluoro-3-trifluoromethylaniline, prepared according to G.C. Finger and colleagues, Journal of Med. Chem., 7, (1964), 572, are added a little at a time, while stirring, to 500 ml of a 2.5 N solution of sulphuric acid heated to a temperature of 65° C. The solution obtained is cooled to 0° C and 27 g of sodium nitrite dissolved in 45 ml of water are added whilst continuing the stirring and ensuring that the temperature does not exceed +5° C. After the end of the addition, the mixture is stirred for a further hour, during which it becomes perfectly clear. Thereafter, whilst carrying out a steam distillation, the cold solution of the diazonium salt is introduced dropwise into a mixture of 56g of copper sulphate, 21 g of urea, 70 ml of water and 2 ml of concentrated sulphuric acid. The speed of addition is regulated so that the phenol formed is immediately carried away. The distillate is cooled and is extracted repeatedly with ether. The ether solutions are combined and dried, the solvent is driven off and the residue is rectified. 37 g (yield: 52%) of 4-fluoro-3-trifluoromethyl-phenol, distilling at 84° C under 15 mm, are obtained.

Analysis: C$_7$H$_4$F$_4$O; (180.10). Calculated %: C 46.48, H 2.23. Found %: 46.42, 2.26.

b. 35 g (0.194 mol) of 4-fluoro-3-trifluoromethyl-phenol diluted with 20 ml of methanol are added slowly to a solution of 10.5 g (0.194 mol) of sodium methylate in 50 ml of methanol. 50.8 g (0.19 mol) of methyl 2-bromo-2-p-chlorophenyl-acetate, diluted with 10 ml of methanol, are introduced a little at a time into the mixture obtained, whilst stirring. The reaction mixture is heated at the reflux temperature for 8 hours, the methanol is evaporated under reduced pressure, water is added to the residue and the mixture is extracted with ether. The aqueous layer is separated off, the organic phase is washed with a sodium bicarbonate solution and then with water, the ether solution is dried, the ether is evaporated and the residue is rectified under reduced pressure.

59.3 g (yield: 86%) of methyl 2-(4-chloro-phenyl)-2-(4-fluoro-3-trifluoromethyl-phenoxy)-acetate are obtained as a viscous oil which passes over at 160° C/0.06 mm.

Analysis: C$_{16}$H$_{11}$ClF$_4$O$_3$ (362.71) Calculated %: C 52.98, H 3.05, Cl 9.77. Found %: 53.04, 3.14, 9.70, 53.24, 3.06.

EXAMPLE 2.

Methyl 2-(4-chloro-phenyl)-2-(4-chloro-3-trifluoromethyl-phenoxy)-acetate.

[X = Cl; Y = Cl; R = CH$_3$O; code number: SL-C.128]

Using the method described in Example 1/b but using 4-chloro-3-trifluoromethyl-phenol, methyl 2-(4-chlorophenyl)-2-(4-chloro-3-trifluoromethyl-phenoxy)-acetate is obtained in a yield of 77%; the compound distils at 150°/0.04 mm and crystallises from pentane. Melting point = 58° C.

Analysis: C$_{16}$H$_{11}$Cl$_2$F$_3$O$_3$, (379.165). Calculated %: C 50.68, H 2.92, Cl 18.70. Found %: 50.72, 3.00, 18.68.

EXAMPLE 3.

2-(4-Chloro-phenyl)-2-(4-fluoro-3-trifluoromethyl-phenoxy)-acetic acid.

[X = F; Y = Cl; R = OH; code number: SL-C.151]

59.3 g (0.163 mol) of methyl 2-(4-chloro-phenyl)-2-(4-fluoro-3-trifluoromethyl-phenoxy)-acetate are added to a solution of 15 g of sodium hydroxide in 400 ml of water. The suspension obtained is stirred and heated at the reflux temperature until a limpid solution is obtained (duration, 4 hours). The reaction mixture is cooled and acidified with a hydrochloric acid solution; an oil precipitates, which is extracted with ether. The ether phase is washed with water and dried and the solvent is driven off. The residue is triturated in petroleum ether until it crystallises, and is recrystallised from a mixture of hexane and cyclohexane (50-50). 43 g (yield: 75%) of 2-(4-chlorophenyl)-2-(4-fluoro-3-trifluoromethyl-phenoxy)-acetic acid are thus obtained. Melting point = 106° C.

Analysis: C$_{15}$H$_9$ClF$_4$O$_3$, (348.68). Calculated %: C 51.67, H 2.60. Found %: 51.90, 2.72, 51.72, 2.67.

Acid equivalent Calculated: 348.68. Found: 347.8.

EXAMPLE 4.

2-(4-Chloro-phenyl)-2-(4-chloro-3-trifluoromethyl-phenoxy)-acetic acid.

[X = Cl; Y = Cl; R = OH; code number: SL-C.127]

Following the procedure of Example 3, but employing methyl 2-(4-chloro-phenyl)-2-(4-chloro-3-trifluoromethylphenoxy)-acetate, 2-(4-chloro-phenyl)-2-(4-chloro-3-trifluoromethyl-phenoxy)-acetic acid is obtained in a yield of 69%. It is recrystallised from a mixture of hexane and benzene (95-5). Melting point = 132° C.

Analysis: C$_{15}$H$_9$Cl$_2$F$_3$O$_3$, (365.13). Calculated %: C 49.34, H 2.48, Cl 19.41. Found %: 49.43, 2.62, 19.48.

EXAMPLE 5.

2-Acetylamino-ethyl 2-(4-chloro-phenyl)-2-(4-fluoro-3-trifluoromethyl-phenoxy)-acetate.

[X = F; Y = Cl; R = OCH$_2$CH$_2$NHCOCH$_3$; code number: SL-C.149]

a. 11.45 g (0.096 mol) of freshly distilled thionyl chloride are added to a suspension of 28.65 g (0.077 mol) of 2-(4-chloro-phenyl)-2-(4-fluoro-3-trifluoromethyl-phenoxy)-acetic acid in 35 ml of dry chloroform. The mixture is stirred for 30 minutes at ambient temperature and is then heated at the reflux temperature until all the acid has dissolved (about 6 hours). The solution is evaporated to dryness under reduced pressure and 2-(4-chlorophenyl)-2-(4-fluoro-3-trifluoromethyl-phenoxy)-acetyl chloride is obtained in the form of an oil, which is used without further purification for the next stage of the synthesis.

b. The acid chloride prepared in a) is dissolved in 35 ml of ether and the solution obtained is added dropwise, whilst stirring and maintaining the temperature at +5° C, to a mixture of 7.98 g (0.077 mol) of N-(2-hydroxyethyl)-acetamide, 7 ml of dry pyridine and 80 ml of dimethylformamide. After the completion of the addition, the stirring is continued for 1 hour at +5° C and then for 4 hours whilst allowing the reaction mixture to return to ordinary temperature. The mixture is then left for 12 hours. It is washed with water and extracted with ether, the ether solution is dried and the solvent is driven off. Finally, an oily residue is obtained, which is triturated in petroleum ether until it crystallises, and is recrystallised from isopropyl alcohol. 23.4 g (yield: 70%) of 2-acetylaminoethyl 2-(4-chloro-phenyl)-2-(4-fluoro-3-trifluoromethylphenoxy)-acetate melting at 108° C are thus obtained.

Analysis: $C_{19}H_{16}ClF_4NO_4$, (433.79). Calculated %: 52.60, H 3.71, N 3.22, F 17.51. Found %: 52.65, 4.04, 3.23, 17.32 52.71, 4.00, 3.11, 17.88.

EXAMPLE 6.

2-Acetylamino-ethyl 2-(4-chloro-phenyl)-2-(4-chloro-3-trifluoromethyl-phenoxy)-acetate.

[X = Cl; Y = Cl; R = $OCH_2-CH_2NHCOCH_3$; code number: SL-C.126]

Following the procedure of Example 5, but using 2-(4-chloro-phenyl)-2-(4-chloro-3-trifluoromethyl-phenoxy)acetic acid, 2-(4-chloro-phenyl)-2-(4-chloro-3-trifluoromethyl-phenoxy)-acetyl chloride, an oily liquid, and 2-acetylamino-ethyl 2-(4-chloro-phenyl-2-(4-chloro-3-trifluoromethyl-phenoxy)-acetate (yield: 59%) are obtained successively; the latter compound, recrystallised from a mixture of ether and isopropyl alcohol (95-5), melts at 110° C.

Analysis: $C_{19}H_{16}Cl_2F_3NO_4$, (450.24). Calculated %: C 50.68, H 3.58, Cl 15.74. Found %: 50.93, 3.87, 15.73.

EXAMPLE 7.

Ethyl 2-(4-chloro-phenyl)-2-(4-fluoro-3-trifluoromethyl-phenoxy)-acetate.

[X = F; Y = Cl; R = $C_2H_5O$; code number: SL-C.150]

A mixture of 15 g (0.043 mol) of 2-(4-chlorophenyl)-2-(4-fluoro-3-trifluoromethyl-phenoxy)-acetic acid, 30 ml of ethanol and 0.5 ml of concentrated sulphuric acid is heated for 6 hours at the reflux temperature. The excess ethanol is evaporated and the residue is washed with water and then with a sodium bicarbonate solution and is dissolved in ether. The ether solution is washed with water and dried, the ether is evaporated and the residue is rectified. 12.65 g (yield: 78%) of ethyl 2-(4-chloro-phenyl)-2-(4-fluoro-3-trifluoromethyl-phenoxy)-acetate, which passes over at 150°/0.07 mm, are thus obtained.

Analysis: $C_{17}H_{13}ClF_4O_3$ (376.73) Calculated %: C 54.19, H 3.47, Cl 9.40, F 20.16. Found %: 54.10, 3.39, 9.40, 20.14, 53.98, 3.38, 20.07.

This ester is also prepared in accordance with the method of Example 1, using ethyl 2-bromo-2-(4-chloro-phenyl)-acetate.

EXAMPLE 8.

2-(4-Fluoro-3-trifluoromethyl-phenoxy)-2-(4-chloro-phenyl)-N-(2-hydroxy-ethyl)-acetamide.

[X = F; Y = Cl; $R_3$ = $-NH-CH_2-CH_2-OH$; code number: SL-D.064]

15.78 g (0.043 mol) of 2-(4-fluoro-3-trifluoromethyl-phenoxy)-2-(4-chloro-phenyl)-acetyl chloride diluted with 15 ml of anhydrous ether are added dropwise, whilst stirring, to a mixture of 12 g (0.19 mol) of mono-ethanolamine and 50 ml of anhydrous ether, cooled in a bath of ice and salt. The mixture is allowed to return to ambient temperature and stirring is continued for a further hour. The mixture is left to stand overnight and, after addition of water, is extracted with ether. The phases are separated and the ether phase is washed with a normal sodium hydroxide solution and then repeatedly with water; it is dried over magnesium sulphate, the solvent is evaporated and the residual oil is caused to crystallise by trituration is petroleum ether.

15 g (yield = 89%) of 2-(4-fluoro-3-trifluoromethyl-phenoxy)-2-(4-chloro-phenyl)-N-(2-hydroxy-ethyl-)acetamide, melting at 95°, are thus obtained.

Analysis: Calculated %: C 52.15, H 3.60, N 3.58. Found %: 52.16, 3.43, 3.50, 52.10, 3.53, 3.59.

The NMR spectrum is in agreement with the structure.

EXAMPLE 9

1-Acetylamino-ethyl 2-(4-fluoro-3-trifluoromethyl-phenoxy)-2-(4-fluoro-phenyl)-acetate.

[X = F; Y = F; R =

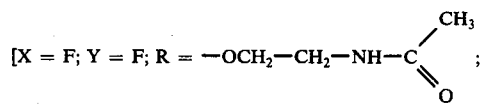

code number: SL-D.097]

A mixture of 5.20 g (0.051 mol) of 2-acetamidoethanol, 49 ml of anhydrous dimethylformamide and 4.6 ml of pyridine is cooled in a bath of ice and salt. 17.88 g (0.051 mol) of 2-(4-fluoro-3-trifluoromethyl-phenoxy)-2-(4-fluoro-phenyl)-acetyl chloride are added dropwise, the mixture is allowed to return to ambient temperature whilst being stirred, stirring is continued for 1 hour, the mixture is left to stand overnight, water is added and the whole is extracted with ether. The ether phase is washed with water and then dried over magnesium sulphate. The solvent is evaporated and the solid residue is triturated with petroleum ether, filtered off and recrystallised from isopropyl ether.

14.1 g (yield = 67%) of 2-acetylamino-ethyl 2-(4-fluoro-3-trifluoromethyl-phenoxy)-2-(4-fluoro-phenyl-)acetate, melting at 100°, are thus obtained.

Analysis:

Calculated %: C 54.68; H 3.86; N 3.36. Found %: 54.64, 3.85, 3.76, 54.73, 3.44, 3.33.

The NMR spectrum confirmed the structure of the compound.

EXAMPLE 10.

1-Methyl-piperidinyl-4 2-(4-fluoro-3-trifluoromethyl-phenoxy)-2-(4-chloro-phenyl)-acetate and its hydrochloride

[X = F; Y = Cl; R =

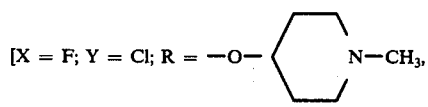

code number: SL-D.123]

A mixture of 9.90 g (0.086 mol) of 4-hydroxy-1-methyl-piperidine and of 50 ml of anhydrous ether is cooled in a bath of ice and salt, and 15.78 g (0.043 mol) of 2-(4-fluoro-3-trifluoromethyl-phenoxy)-2-(4-chlorophenyl)acetyl chloride diluted with 15 ml of the same solvent are then added dropwise whilst stirring. The mixture is allowed to return to ambient temperature and is stirred for a further hour and then left to stand overnight, water is added and the oily layer is extracted with ether. The ether phase is washed repeatedly with water and dried over magnesium sulphate, and the solvent is evaporated. An oily base base is obtained, which is directly converted to the salt by adding a solution of hydrogen chloride gas in isopropanol. 17 g of 1-methyl-piperidinyl-4 2-(4-fluoro-3-trifluoromethyl-phenoxy)-2-(4-chloro-phenyl)-acetate hydrochloride, melting at 170° after recrystallisation from isopropanol, are thus obtained.

Analysis: Calculated %: C 52.30, H 4.39, N 2.90, Cl- 7.35 Found %: 52.30, 4.42, 2.93, 7.36 52.39, 4.53, —, 7.36
The NMR spectrum corresponds to the structure.

EXAMPLE 11.

N,N-Dimethyl-3-aminocarbonyl-propyl 2-(4-fluoro-3-trifluoromethyl-phenoxy)-2-(4-chloro-phenyl)-acetate.

[X=F; Y=Cl; R =

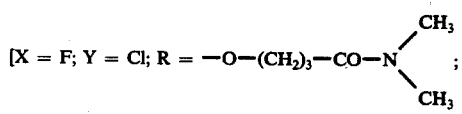

code number: SL-D.126]

A mixture of 5.45 g (0.0473 mol) of 4-hydroxy-N,N-dimethyl-butyramide, 65 ml of anhydrous tetrahydrofurane and 4,36 g (0.0431 mol) of anhydrous triethylamine is cooled in a bath of ice and salt. 15.78 g (0.043 mol) of 2-(4-fluoro-3-trifluoromethyl-phenoxy)-2-(4-chloro-phenyl)-acetyl chloride are added dropwise whilst stirring and ensuring that the temperature does not exceed 0°. The mixture is allowed to return to ambient temperature, stirred for a further two hours and left to stand overnight, the triethylamine hydrochloride which has precipitated is filtered off, the solvent is evaporated from the filtrate and the residue is taken up in ether. The ether solution is washed with water and dried over magnesium sulphate, and the solvent is evaporated. This gives 17 g of 3-N,N-dimethylaminocarbonyl-propyl-1 2-(4-fluoro-3-trifluoromethyl-phenoxy)-2-(4-chloro-phenyl)-acetate in the form of an oil which decomposes on distillation and which is purified by chromatography on silica. Finally, 11 g (yield = 55%) of pure substance are obtained.

Analysis:
Calculated %: C 54.61, H 4.36, Cl 7.68, N 3.03. Found %: 54.63, 4.58, 7.60, 3.08, 54.82, —, 7.61, 3.16.
The NMR spectrum confirmed the structure of the compound.

EXAMPLE 12.

3,3,5-Trimethyl-cyclohexyl-1 2-(4-fluoro-3-trifluoromethyl-phenoxy)-2-(4-chloro-phenyl)-acetate

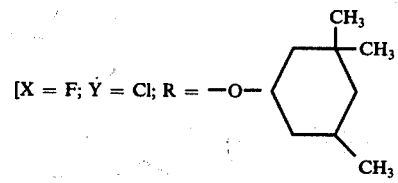

code number: SL-S.128]

15 g (0.043 mol) of 2-(4-fluoro-3-trifluoromethyl-phenoxy)-2-(4-chloro-phenyl)-acetic acid, 9.17 g (0.0645 mol) of 3,3,5-trimethyl-cyclohexanol-1, 0.129 g of p-toluenesulphonic acid and 35 ml of xylene are introduced into an Erlenmeyer flask equipped with a magnetic stirrer, a Dean and Stark device and a reflux condenser. The mixture is heated at the reflux temperature for about 6 hours and is then cooled. The xylene solution is washed with a 20% strength sodium hydroxide solution and then repeatedly with water and is dried over magnesium sulphate, the solvent is evaporated from the filtrate and the oily residue is rectified.

3,3,5-Trimethyl-cyclohexyl-1 2-(4-fluoro-3-trifluoromethyl-phenoxy)-2-(4-chloro-phenyl)-acetate is obtained in the form of an oil which passes over at 180°/0.05 mm and which is crystallised from a mixture of ethanol and water (90-10). Melting point =49°. Yield = 60%.

Analysis: Calculated %: C 60.96, H 5.33, N 7.50. Found %: 60.81, 5.08, 7.48, 61.05, 4.97, 7.41.
The NMR spectrum confirms the structure of the compound.

The compounds of Examples 1 to 12 and other compounds which are prepared in the same manner are listed in Table I.

Table I

| Example | Code | X | Y | R | Characteristics (° C) |
|---|---|---|---|---|---|
| 1 | SL-C.248 | F | Cl | CH$_3$O | B.p. 160/0,6 mm |
| 2 | SL-C.128 | Cl | Cl | CH$_3$O | B.p. 150/0,4 mm |
| 3 | SL-C.151 | F | Cl | OH | M.p. 106 |
| 4 | SL-C.127 | Cl | Cl | OH | M.p. 132 |
| 5 | SL-C.149 | F | Cl | CH$_3$CONHCH$_2$CH$_2$O | M.p. 108 |
| 6 | SL-C.126 | Cl | Cl | CH$_3$CONHCH$_2$CH$_2$O | M.p. 110 |
| 7 | SL-C.150 | F | Cl | C$_2$H$_5$O | B.p. 150/0,07 mm |
| 8 | SL-D.064 | F | Cl | OHCH$_2$—CH$_2$—NH | M.p. 95 |
| 9 | SL-D.097 | F | F | CH$_3$CONHCH$_2$CH$_2$O | M.p. 100 |

Table I-continued

| Example | Code | X | Y | R | Characteristics (° C) cl = hydrochloride |
|---|---|---|---|---|---|
| 10 | SL-D.123 | F | Cl | CH₃—N⟨piperidine⟩—O | M.p. 170 |
| 11 | SL-D.126 | F | Cl | (CH₃)₂N—CO—(CH₂)₃—O | |
| 12 | SL-D.128 | F | Cl | 3,3,5-trimethylcyclohexyl—O | M.p. 49 |
| 13 | SL-D.063 | F | Cl | NH₂ (on pyridine-CH₂—O—) | M.p. 100 |
| 14 | SL-D.065 | F | Cl | pyridine-CH₂—O— | M.p. (cl) 135 |
| 15 | SL-D.095 | F | F | OH | M.p. 116 |
| 16 | SL-D.096 | F | F | CH₃O | B.p. 125–130/0,5 mm |
| 17 | SL-D.124 | F | Cl | C₂H₅—COOCH₂O | B.p. 152–155/0,2 mm |
| 18 | SL-D.125 | F | Cl | 2,2-dimethyl-1,3-dioxolan-4-yl-CH₂—O | B.p. 155–160/0,02 mm |
| 19 | SL-D.127 | F | Cl | (C₂H₅)₂N—CH₂—CH₂O | M.p. (cl) 126 |

The compounds of the invention were subjected to a series of pharmacological tests intended to demonstrate their effects on the content of lipids (triglycerides and cholesterol) in the blood. The reference substances chosen were clofibrate or ethyl 2-p-chlorophenoxy-2-methyl-propionate, and halofenate or 2-acetamido-ethyl 2-p-chlorophenyl-2-m-trifluoromethylphenoxy-acetate.

METHOD.

The acute toxicity was studied by oral administration to CD1 mice of both sexes. The 50% lethal doses (LD 50) were determined graphically.

The hypocholesterolaemic action was determined on male albino rats of the CD1 race (Charles River) weighing on average 250 g and fed normally, the rats being divided into batches each of 10 animals. Daily doses of one of the compounds studied were administered orally for 7 days. On the 8th day, the contents of cholesterol and triglycerides in the blood were determined and compared with those of animals of the untreated comparison group. In this way it was possible graphically to evaluate, for each compound, the 30% active dose (AD 30), that is to say the daily dose which causes a 30% reduction in the content of cholesterol or of triglycerides in the serum.

RESULTS

Table II summarises the results obtained with the reference substances and the compounds of the invention chosen by way of examples.

Table II

| Compound | Acute toxicity in mice on oral administration LD 50, mg/kg | Hypolipaemic activity in rats on oral administration AD 30 (in mg/kg) | |
|---|---|---|---|
| | | Cholesterol | Triglycerides |
| SL C 149 | 2,000 | 17 | 12 |
| SL C 150 | >2,500 | 20 | 25 |
| SL C 151 | 2,000 | 50 | 12 |
| SL D 063 | >2,000 | >100 | 20 |
| SL D 064 | >2,000 | >100 | 20 |
| SL D 065 | >2,000 | 55 | 35 |
| SL D 097 | >2,000 | >100 | 25 |
| Halofenate | 1,800 | 70 | 50 |
| Clofibrate | 1,300 | 160 | 200 |

*AD 30 = daily dose which causes a 30% reduction in the content of cholesterol or of triglycerides in the serum.

In a second series of experiments, the experimental technique was modified slightly: the compounds studied are dispersed in olive oil instead of being dissolved in water.

Table III

| Compound | Acute toxicity in mice on oral administration LD 50, (mg/kg) | Hypolipaemic activity in rats on oral administration AD 30 (in mg/kg) | |
|---|---|---|---|
| | | Cholesterol | Triglycerides |
| SL-D.123 | >2,000 | 50 | 20 |
| SL-D.126 | >2,000 | 70 | 20 |
| SL-D.128 | >2,000 | 80 | 10 |
| SL-C.149 | 2,000 | 30 | 20 |

*AD 30 = daily dose which causes a 30% reduction in the content of cholesterol or of triglycerides in the serum.

These results show that the compounds of the invention, whilst being less toxic than the reference substances, have a hypolipaemic and hypocholesterolaemic effect much superior to that of the latter. SL-C-149, in particular, is four times more active than halofenate and about 15 times more active than clofibrate.

The therapeutic index of the compounds of the formula (I) is excellent.

The preceding results show that the compounds of the invention are suitable for the treatment of disturbances of the lipid metabolism, especially of atherogenic hyperlipaemias.

The invention consequently comprises all pharmaceutical compositions which contain the compounds (I) as active principles, in an effective amount in combination with any compatible, pharmaceutically acceptable carrier, e.g. for endo-rectal, parenteral and, more especially, oral administration. These pharmaceutical compositions can also contain other medicaments with which the compounds of formula (I) are pharmaceutically and therapeutically compatible.

For oral administration, any pharmaceutical form suitable for this method of administration may be used, that is to say tables, dragees, gelatin-coated pills, capsules, cachets and potable solutions or suspensions, and the unit dose of the compound of formula (I) can vary between 10 and 250 mg, whilst a daily dose is between 20 and 1,500 mg.

For endo-rectal administration, suppositories containing 20 to 400 mg of compound (I) and administered to the patient at the rate of one to four per twenty four hours may be used.

For parenteral administration, sterile injectable solutions prepared beforehand or at the time of use, and buffered to a physiological pH, may be used. These solutions may contain 3 to 150 mg of active principle in a volume of 1 to 5 ml. In practice, they are divided into ampoules of 1 to 5 ml contents for intramuscular or intravenous administration or for administration by slow intravenous infusion. The daily dose administered parenterally can vary between 3 and 900 mg.

We claim:
1. 1-Acetylamino-ethyl 2-(4-chloro-phenyl)-2-(4-fluoro-3-trifluoromethyl-phenoxy)-acetate.
2. A pharmaceutical composition having a hypolipaemic and hypocholesterolaemic effect comprising, in association with a compatible pharmaceutically acceptable carrier, an effective amount of a compound as claimed in claim 1 to provide said hypolipaemic and hypocholesterolaemic effect.
3. 2-Acetylamino-ethyl 2-4(chloro-phenyl)-2-(4-chloro-3-trifluoromethyl-phenoxy)-acetate.
4. A pharmaceutical composition having a hypolipaemic and hypocholesterolaemic effect comprising, in association with a compatible pharmaceutically acceptable carrier, an effective amount of a compound as claimed in claim 3 to provide said hypolipaemic and hypocholesterolaemic effect.

* * * * *